March 12, 1963 C. FISCHER Plant Pat. 2,235
GLADIOLUS PLANT
Filed April 12, 1962
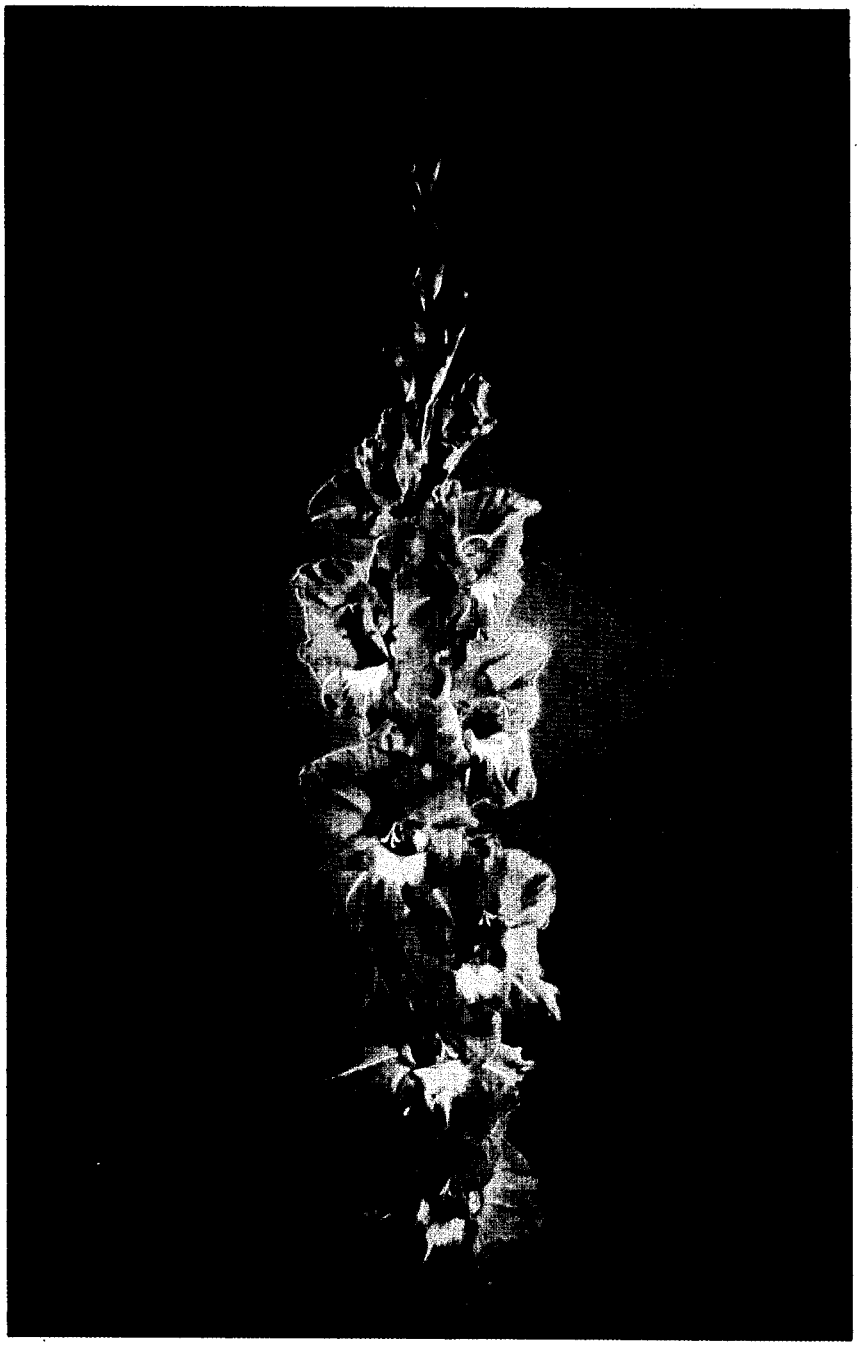
Inventor.
Carl Fischer
By: Robb & Robb
Attorneys United States Patent Office Plant Pat. 2,235
Patented Mar. 12, 1963

2,235
GLADIOLUS PLANT

Carl Fischer, St. Charles, Minn., assignor to Imperial Flowers Limited, Leamington, Ontario, Canada, a corporation of Canada Filed Apr. 12, 1962, Ser. No. 187,142
1 Claim. (Cl. 47—60)

The present invention relates to a new and distinct variety of gladiolus plant which was originated by me by crossing the variety "Fire Opal" (unpatented) with the variety "Dusk" (unpatented), the former being the seed parent, and the latter being the pollen parent.

The primary objective of this breeding was to produce a new early red gladiolus variety suitable for the markets in the northern areas of this country. This objective was fully achieved, along with other desirable features, as evidenced by the following unique combination of characteristics which are outstanding in the new variety and which distinguish it from its parents, as well as from all other varieties of which I am aware:

(1) An extremely vigorous and rugged habit;
(2) An early blooming habit;
(3) A prolific blooming habit;
(4) A butterfly-type flower form;
(5) Good resistance to hot weather; and
(6) A distinctive and attractive general color tonality of the flowers which are characterized by various shades of red color with white blotches.

My new variety resembles the variety known as "Leah Gorham" (unpatented) more than any other known variety, but differs therefrom principally by being a faster propagator; healthier, larger and taller; earlier in blooming habit; more ruffled and needle-pointed flowers; and more rose-red in flower color.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows a typical specimen flower spike of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations from cormels.

*Plant*

Growth: Extremely rugged; prolific propagator; blossom spike attains height averaging from 62 inches to 64 inches.

Blooming habit: Very early bloomer in the northern latitudes of the United States; comes into bloom from the planting of large bulbs in about 65 days.

Stems: Straight and willowy.
*Diameter at base.*—⅜ inch.
*Color (just above the bulb).*—Light rose purple.

Foliage: Slender; upright; attains height of about 40 inches to 42 inches; leaves average 1¼ inches wide. Color—healthy green.

Disease resistance: Unusually resistant to Fusarium yellows, sclerotina dry rot and Septoria leaf spot, as determined by comparison with other varieties grown in my fields near St. Charles, Minnesota, in irrigated black loam soil.

Corms (bulbs): Round; plump; with thin, glossy husk. Color of flesh—Apricot, Plate 609/1.

*Flower*

Spike: Tall; willowy; bears from 16 to 18 buds, with from 5 to 7 buds opening simultaneously and showing color at same time; flower head about 24 inches long.

Bud:
*Size.*—About 2½ inches long when opening.
*Opening.*—From 5 to 7 buds show color at one time.

Flower:
*Arrangement.*—Florets are informally arranged on the stem, and occasionally the lower florets are misplaced.
*Size.*—Individual florets average about 5 inches in diameter; upper blooms progressively smaller.
*Form.*—Florets are butterfly-shaped, ruffled and needle-pointed.
*Keeping qualities.*—Flowers should be cut in loose bud stage, or with one or two bottom florets open, in order to open and keep well.

Petals:
*Shape.*—Intensely ruffled; winged; recurved; some are needle-pointed.
*Size.*—Outer petals—2½ inches wide. Lip petal—1½ inches wide.
*Aspect.*—Heavy substance; smooth surface.
*Fragrance.*—None.
*Color.*—Face of flower generally is Oriental Red, with tips of petals being Oriental Red, Plate 819/1, shading from Oriental Red, Plate 819/2 to Oriental Red, Plate 819/3, and further shading to Geranium Lake, Plate 20/2 at heart of flower; flowers have pure white blotch and midrib, with blotch edged with Oriental Red, Plate 819/3; reverse of florets generally is Oriental Red, Plate 819/1; florets have some purple color at calyx.

*Reproduction Organs*

Stamens: Color—purple.
Pistil: Color—Gernaium Lake, Plate 20/3.

I claim:

A new and distinct variety of gladiolus plant, substantially as herein shown and described, characterized particularly as to novelty by the unique combination of an extremely vigorous and rugged habit, an early blooming habit, a prolific blooming habit, a butterfly-type flower form, good heat resistance, and a distinctive and attractive general color tonality of the flowers which are basically Oriental Red with white blotches.

No references cited.